(12) United States Patent
Easterling et al.

(10) Patent No.: US 6,525,100 B1
(45) Date of Patent: Feb. 25, 2003

(54) COMPOSITION AND METHOD FOR TREATING PEYRONIE'S DISEASE AND RELATED FIBROTIC TISSUE DISORDERS

(76) Inventors: W. Jerry Easterling, 8400 Blanco Rd., Suite 204, San Antonio, TX (US) 78216; William P. Fitch, III, 8038 Wurzbach #430, San Antonio, TX (US) 78229

( * ) Notice: Subject to any disclaimer, the term of this patent is extended or adjusted under 35 U.S.C. 154(b) by 0 days.

(21) Appl. No.: 09/721,439

(22) Filed: Nov. 22, 2000

Related U.S. Application Data

(63) Continuation-in-part of application No. 09/411,175, filed on Oct. 1, 1999, which is a continuation-in-part of application No. 09/128,103, filed on Aug. 3, 1998, now Pat. No. 6,031,005.

(51) Int. Cl.$^7$ .............................. A61K 31/54; A61K 9/70
(52) U.S. Cl. ...................... 514/654; 514/34; 514/225.5; 424/447; 424/443; 424/430
(58) Field of Search .................................. 424/430, 447, 424/443; 514/34, 225.5, 654

(56) References Cited

U.S. PATENT DOCUMENTS

| | | | |
|---|---|---|---|
| 4,338,300 A | | 7/1982 | Gelbard |
| 4,777,171 A | * | 10/1988 | Beitner ..................... 514/225.5 |
| 5,104,858 A | * | 4/1992 | Hait et al. ..................... 514/34 |
| 5,139,944 A | | 8/1992 | Sawyer |
| 5,242,391 A | | 9/1993 | Place |
| 5,474,535 A | | 12/1995 | Place |
| 5,569,678 A | | 10/1996 | Lee |
| 5,731,339 A | | 3/1998 | Lowrey |
| 5,750,141 A | | 5/1998 | Roberts |
| 5,773,020 A | | 6/1998 | Place |
| 5,902,609 A | | 5/1999 | Lee |
| 6,113,939 A | * | 9/2000 | Place et al. .................. 424/430 |

FOREIGN PATENT DOCUMENTS

| | | |
|---|---|---|
| WO | WO 91/01624 | 2/1991 |
| WO | WO 94/02130 | 2/1994 |
| WO | WO 94/17839 | 8/1994 |
| WO | WO 96/29987 | 8/1996 |

OTHER PUBLICATIONS

Levine, et al., "Intralesional Verapamil Injection for the Treatment of Peyronies Disease"; Journal of Urology; vol. (151, 1522–1524; 1994.
Levine; "Treatment of Peyronie's Disease With Intralesional Verapamil Injection"; Journal of Urology; vol. 158, 1395–1399; 1997.
Rehman, et al.; "Use of Intralesional Verapamil to Dissolve Peyronie's Disease Plaque: A Long–Term Single–Blind Study"; Urology, vol. 51, 620–626; 1998,
Willmann et al.; "Lecithin Organo Gel as Matrix for Transdermal Transport of Drugs"; Journal Of Pharmaceutical Science; vol. 81, No. 9; 1992.
Riedl et al.; "Iontophoresis for The Treatment of Peyronie's Disease"; Journal of Endourology, vol. Suppl 1; 1997.
Sekine et al.; "Gel Ointment of Verapamil For Percutaneous Absorption"; Drug Design and Delivery 1 (3): 245–52; 1987.
Jain et al.; "In Vitro Percutaneous Absorption of Verapamil"; Indian Journal of Experimental Biology 34(5): 475–7; 1996.
Verapamil. The Merck Index (12th Edition); Entry N° 10083; 1996.

\* cited by examiner

*Primary Examiner*—Jose' G. Dees
*Assistant Examiner*—Mina Haghighatian
(74) *Attorney, Agent, or Firm*—David G. Henry

(57) ABSTRACT

The invention is of a topical medicament and associated methodology for use thereof, through the use of which Peyronie's disease may be effectively, cost effectively, and painlessly treated. The primary active ingredient is a calmodulin blocker, the preferred such ingredient being trifluroperizine.

4 Claims, No Drawings

COMPOSITION AND METHOD FOR TREATING PEYRONIE'S DISEASE AND RELATED FIBROTIC TISSUE DISORDERS

This application is a CIP of Ser. No. 09/411,475 filed Oct. 1, 1999 which is a CIP of Ser. No. 09/128,103 filed Aug. 3, 1998, now U.S. Pat. No. 6,031,005.

BACKGROUND OF THE INVENTION

1. Field of the Invention

Applicant's invention relates to medicaments and treatment procedures relating to fibrotic tissue maladies.

2. Background Information

A. Peyronie's Disease

The initial focus of the present invention—Peyronie's disease—has likely plagued men for time immemorial, but has been recognized as a distinct malady for no less than 400 years. Peyronie's disease was first described in 1743 by a French surgeon, Francois de la Peyronie. The disease was written about as early as 1687 and was oftentimes associated with impotence.

Peyronie's disease manifests itself in various manners, and to varying degrees of severity. The most common manifestation of Peyronie's disease is in the form of a "lump," "plaque" or "hard" area in the non-erect penis. With or without these palpable symptoms, painful erections and penile disfigurement are often associated with the malady.

The pain and disfigurement associated with Peyronie's disease relate to the physical structure of the penis in which is found two erectile rods, called the corpora cavernosa, a conduit (the urethra) through which urine flows from the bladder, and the tunica which separates the cavernosa from the outer layers of skin of the penis. A person exhibiting Peyronie's disease will have formation(s) of plaque or scar tissue between the tunica and these outer layers of the skin. The scarring or plaque accumulation of the tunica reduces its elasticity causes such that, in the affected area, it will not stretch to the same degree (if at all) as the surrounding, unaffected tissues. Thus, the erect penis bends in the direction of the scar or plaque accumulation, often with associated pain of some degree.

Peyronie's disease often occurs in a mild form and heals spontaneously in 6 to 15 months. However, in severe cases, the hardened plaque substantially reduces penile flexibility and causes excruciating pain as the penis is forced into a highly arcuate or even serpentine configuration. A plaque on the top of the shaft (most common) causes the penis to bed upward; a plaque on the underside causes it to bend downward. In some cases, the plague develops on both top and bottom, leading to indentation and shortening of the penis.

In all but minor manifestations of Peyronie's disease, the victim has some degree of sexual dysfunction. In more severe cases, sexual intercourse is either impossible, or is so painful as to be effectively prohibitive.

While plaque of Peyronie's disease is itself benign, or noncancerous, this is of little solace to sufferers of the disease.

Reports indicate an incidence of Peyronie's disease in no less than approximately one percent, to as high as three percent, of the male population. Although the disease occurs mostly in middle-aged men, younger and older men can acquire it. About 30 percent of men with Peyronie's disease also develop fibrosis (hardened cells) in other elastic tissues of the body, such as on the hand or foot. A common example of such a condition is known as Dupuytren's contracture of the hand.

Many researchers believe the plaque of Peyronie's disease develops following trauma to the penis (hitting or bending) that causes localized bleeding inside the penis. If the penis is abnormally bumped or bent, an area where the septum attaches to the elastic fibers surrounding the corpora cavernosa may stretch beyond its normal limit, injuring the lining of the erectile chamber and, for example, rupturing small blood vessels. Also, as a result of aging, diminished elasticity near the point of attachment to the septum may tend to increase the chances of injury of this nature.

Such a damaged area may heal slowly or abnormally because of repeated trauma to the same area and/or because of the natural, minimal amount of blood-flow in the sheath-like fibers of the elastic structures of the penis. In cases of Peyronie's disease which tend to heal within about a year, the plaque does not tend to advance beyond an initial inflammatory phase. In cases that persist for longer periods, the plaque typically undergoes fibrosis, or the formation of tough fibrous tissue, and even calcification, or the formation of calcium deposits.

While trauma might explain acute cases of Peyronie's disease, it does not explain why most cases develop slowly and with no apparent traumatic event. It also does not explain why some cases disappear quickly, and why similar conditions, such as Dupuytren's contracture, do not seem to result from severe trauma.

In some cases, men who are related by blood tend to develop Peyronie's disease, which suggests a possible genetic predisposition to Peyronie's disease.

B. Present Treatment

Until recently, the treatment of Peyronie's disease was on a largely experimental basis. This was because the cause(s) and development of Peyronie's disease were not well enough understood to provide effective relief and treatment.

Until recently, surgery was the only approach to treating Peyronie's disease which appeared to have predictably repeatable efficacy. Surgery was, however, usually only indicated in long-term cases where the disease was stabilized and the deformity prevents intercourse and/or causes extreme pain. However, complications can and do often develop from surgery, including a permanent shortening of the penis.

Other approaches to treating Peyronie's disease included simple plaque excision, described in the 19th century by MaClellan, Regnoli and Huitfield. By the early 20th century, however, most experts described this technique as disastrous. For this reason Young developed a procedure that simply "freed" the plaque from the tunica albuginea in order to improve erectile dynamics. Lowsely and Boyce then re-explored the technique of simple plaque excision by adding the interposition of a 'pat-pad' graft into the defect. Although many others continued to report success with this technique, it failed to gain general acceptance as the treatment of choice.

In 1995 Nesbit described the correction of congenital penile curvature with multiple elliptical excisions of the corporeal tunica. To this day, many surgeons prefer this technique for the correction of the Peyronie's bend. However, the inevitable penile shortening led Devine and Horton (1974)to experiment with further grafting procedures. Having experimented with fascial, arterial and venous patches in dogs, they came to the conclusion that dermal grafts were the least likely to "contract" and so reproduce the defect. To this day, many other grafting materials have been tried including autologous vein, temporoparietal fascia, tunica vaginalis, gortex and dacron.

The cost of the various surgical approaches to Peyronie's disease (no less than around $6,500) is, alone, often a deterrent to many Peyronie's disease sufferers in adopting this particular approach to treatment. While surgical intervention was, prior to the present invention, the most likely effective treatment in any given case of Peyronie's disease, the condition does often reappear, even after surgery.

The other, recently advocated, non-surgical approaches to Peyronie's disease treatment are many and varied, although they too were all largely ineffective. Attempts to dissolve the plaques by direct intra-lesional injections have been tried since the late 19th century. Walsham and Spencer injected both mercury and iodide and intra-lesional injections of fibrinolysins were used in the 1820's. Teasley introduced the concept of intra-leasional steroid injections in 1954, although the pain caused by the high injection pressures led many surgeons to perform the procedure under general anesthetic. In 1959 Hinman developed a "high pressure" screw-threaded injection device that was somewhat effective in certain cases, and could be used with no anaesthesia, but still lacked predictable efficacy. More recently, intra-lesional injections of agents such as Verapamil and clostridial collagenase have been tried, but with very limited success.

Of the injection methodologies, those involving clostridial collagenase appear to exhibit the most consistent efficacy, though still quite limited in effect and duration. Collagenase is likely effective through its ability to dissolve collagen, the major component of the plaque of Peyronie's disease.

Both external beam radiation treatment and intra-lesional implantation of radium seeds have been tried since the turn of the 20th century. In 1921, Sonntag reviewed this practice and claimed that these treatments were actively detrimental. Despite this, radiation therapy had been used in many clinics over the years and some authorities still claim that success can be anticipated if a radiation regimen is initiated early in the course of the disease. Radiation treatment is also said to be particularly effective for treating patients whose predominant symptom is pain (as opposed to severe disfigurement).

As technologies have evolved, so have the associated energy sources which have been applied to treat Peyronie's disease. Early in the 20th century, diathermy current was used to generate heat to treat the plaque and eventually low voltage electrical devices were developed and sold for use in the home. Perhaps the most imaginative variant was the technique known as histamine iontophoresis. This combined the use of electrodes with a "plaque busting" solution that was supposedly absorbed into the penis when an electrical gradient was applied. In more recent times, both ultraviolet light and local ultrasound have surfaced and submerged in the treatment history.

Not surprisingly, the inevitable application of laser technology has recently emerged as a means of "vaporizing" the plaque. Again, the efficacy of this latest treatment is open to serious question.

The staggering array of treatment options for Peyronie's disease (failed attempts, really), and the invested effort, cost and intellectual energy which they represent, are testament to the serious need that remains for an effective treatment for Peyronie's disease, and one which patients can tolerate from cost, comfort and convenience perspectives.

All-in-all, until recently, there has simply been no truly effective treatment of Peyronie's disease—a disease which often produces such severe discomfort and distress that sufferers have been willing to endure such treatments as penile injections.

The recent change of fortunes for Peyronie's disease sufferers came in the form of W. Jerry Easterling's invention of a topical verapamil composition which, when applied topically to the penile shaft, proved remarkably effective in "dissolving" Peyronie's plaques. Since the introduction of Mr. Easterling's topical verapamil compositions, the treatment for Peyronie's disease has changed throughout the world. Known prescriptions for the composition have grown at approximately ten percent per month in the year prior to this application, with reported efficacy that eclipses any prior treatment, including even that involving the injecting of verapamil directly into Peyronie's plaque (Levine). Notably, Levine himself has now prescribed Mr. Easterling's composition for the treatment of Peyronie's patients.

Mr. Easterling has also explored (with similar success) the use of topical calcium channel blocker compositions in the treatment of Dupuytren's contracture of the hand and Ledderhose Fibrosis of the foot.

It is proposed that calcium channel blockers (including verapamil), when applied topically, migrate into the collagenous plaque of such fibrotic maladies as Peyronie's disease, Dupuytren's contracture of the hand and Ledderhose Fibrosis of the foot, and block the cellular entry of divalent calcium ions, thereby altering fibroblast metabolism which decreases the production of collagen. Simultaneously the production of collagenase is increased by the maturation of fibroblast collagenase. The collagenase causes degradation and remodeling of the fibrotic plaque. Due to the roles of divalent calcium and zinc in the production of collagenase, the collagenase is classified as a metaloprotease.

As the present inventor came to understand the apparent mechanism of action of calcium channel blockers in the treatment of fibrotic disease states, he postulated that other mechanisms which affect calcium utilization in the body might also be harnessed in the treatment of fibrotic disease states. Initial experimentation indicates that such is the case. Albeit with some side effects which, it is believed, can be alleviated to an acceptable degree with dosage modifications, the use of calmodulin blockers in treating Peyronie's disease has proven efficacious.

SUMMARY OF THE INVENTION

It is an object of the present invention to provide a novel a medicament useful in the treatment of fibrotic tissue disorders, exemplified by Peyronie's disease.

It is another object of the present invention to provide a novel and unobvious medicament useful in the treatment of fibrotic tissue disorders, exemplified by Peyronie's disease, which medicament obviates the need for such dramatic treatments as intra-penile injections and surgery.

It is another object of the present invention to provide a novel and unobvious medicament useful in the treatment of fibrotic tissue disorders, exemplified by Peyronie's disease, which medicament is more effective that existing means for treatment.

In satisfaction of these and related objectives, Applicant's present invention provides a topical medicament and associated methodology for use thereof, through the use of which Peyronie's disease may be effectively, cost effectively, and painlessly treated.

DETAILED DESCRIPTION OF THE PREFERRED EMBODIMENT

The medicament of the present invention is a topical gel which has effected a complete reversal of Peyronie's disease symptoms in a statistically significant number of experimental applications. From these preliminary results, it appears that the same treatment will (like topical verapamil) be effective in the treatment other fibrotic tissue disorders, including Dupuytren's contracture of the hand and Ledderhose Fibrosis of the foot.

The chosen calmodulin blocker for the present medicament is phenothiazine trifluoperazine.

The trifluroperazine topical gel of the present invention is dispensed, via the preferred mode of the present invention, in a 1.0 ml amber syringe which is graduated in 0.01 ml increments, with major graduations at 0.1 through 1.0 ml. The syringe is filled to the 1.0 ml mark with the gel (assuming a 1.0 ml syringe is used).

The single dose of the present Trifluroperazine, gel evaluated thus far contained 20 mg of trifluoperazine, and was contained in 0.5 ml of the gel. However, it is believed that a 20 mg dose is more than is necessary to achieve therapeutic results, and was responsible for certain undesirable side effects. Thus, it is recommended that initial treatment be conducted with individual dosages not in excess of 5 mg, until patient tolerance is evaluated.

Syringes in which the present Trifluroperazine, gel is delivered to patients can be prepared with any number of doses, limited only by the capacity of the syringes.

Each syringe is capped with a removable tip that can be removed and replaced by simply pushing and pulling at the dispensing end of the syringe.

Packaging in which the filled syringes are dispensed to patients (and/or the syringes themselves) should be labeled with the following legend:

This medication must not be refrigerated.

Refrigeration may destroy the absorption qualities of the carrier agents(s).

The patient is to apply 0.5 ml of the present medicament twice each day, preferably in the morning and after a shower (or other cleansing) in the evening. Before each application, any remnant of the prior dose(s) must be completely removed and the area of prior application cleaned and dried before a new dose is applied.

For the first does of each syringe, the patient removes the syringe cap and dispels 0.5 ml by pushing the plunger to the 0.5 ml syringe mark. The second dose requires pushing the plunger to the 0.0 ml syringe mark, and so on. One 1.0 ml syringe will, therefore, last one day according to the preferred mode of practice of the present invention.

Once the medication is dispensed from the syringe, the patient should apply the medication by starting at the point where the plaque is heaviest, or where the curvature begins, and work out until the entire penile shaft has been covered with medication. Absorption is rapid which allows the patient to immediately dress.

Application to the entire penile shaft is important. In initial experimental use of the present medicament, localized application of the gel (solely to areas atop the suspected plaque) effected merely a change in the direction of the previous curvature. Subsequent application to the entire penile shaft in the same patients resulted in complete reversal of symptoms. This phenomena may be explained if plaque, to varying degrees, is present throughout the entire penile shaft, and not just localized to the point(s) of curvature.

During the treatment regimen, each patient's progress should be evaluated, at least weekly. If no results have occurred by the end of the 3rd week, the dose should be increased and the process repeated.

While the initial dose of the preferred trifluroperazine gel has, to date, been 0.5 ml (containing 20 mg of Trifluroperazine) applied twice daily, in the morning and at night, it is suspected that, once a patient receives relief, the plaque may re-form if the medication is stopped. In that event, continued use of the present medicament, perhaps at a lower dose, or less frequently, may be indicated.

Preparation of the trifluroperazine gel (subject to scale-up under mass production conditions) is presently as follows:

I. Trifluoperazine Topical Gel 40 g/ml Preparation Procedure (Prepare 60 mL)

Note: 0.5 ml (20 mg) is applied to the entire penile shaft twice a day.

1. Add 7 mL of sterile water for irrigation to 2.4 Grams of trifluoperazine powder and stir well.
2. using a laboratory heating plate, heat the trifluoperazine solution at 60–70 degrees Centigrade with stirring until a clear solution exists.
3. Add 16 ml of lecithin/isopropyl myristate solution (see preparation below), 2 mL of propylene glycol and stir well.
4. Draw mixture into a 60 mL sterile luer-lock syringe.
5. Draw 34 mL of 20% pluronic organogel (see preparation below) into a second 60 mL sterile luer-lock syringe.
6. Using a luer-lock to luer-lock adapter, mix the two syringes well with force by passing the material back and forth at least 40 times until a homogeneous gel is formed.
7. Package or dispense in amber syringes and protect from light. Store at room temperature.

II. Pluronic Organogel 20% (To Prepare 3000 mL):

1. Add 9 Grams of Potassium Sorbate to 600 Grams of Pluronic F127 (Poloxamer 407) in a calibrated glass vessel capable of containing 4000 mL of water.
2. Bring to final volume (3000 mL) with cold (refrigerated) purified water, USP. Make certain that all the granules are wet.
3. Place mixture in refrigerator and allow to stand until a clear solution exists.
4. Finalize volume to 3000 mL with purified water.
5. Store in refrigerator until ready to use.

III. Lecithin/isopropyl Myristate Solution (To Prepare 2800 mL):

1. Add 1,274 Grams of Lecithin Soya Granular and 8.4 Grams of Sorbic Acid, NF power to a calibrated glass vessel capable of containing 3000 mL of water.
2. Add 1,490 ml of isopropyl Myristate, NF to the above mixture.
3. Allow to stand at room temperature until a liquid of syrup consistency exists.
4. Stir well and store in a light protected glass container.

Although the invention has been described with reference to specific embodiments, particularly with respect to the particular active ingredient of the present medicament, this description is not meant to be construed in a limited sense, in particular to limit the scope of the appended claims to cover only those medicaments and associated modalities of treatment which include trifluroperazine as the calmodulin blocker, the function of which in the area of plaque appears to lie at the heart of the efficacy of the present medicament. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A medicament for topically, transdermally treating subdermal fibrotic tissue accumulation disorders comprising:
   carrier host agent for transdermal delivery of a calmodulin blocker agent to an aberrant fibrotic tissue accumulation;
   a calmodulin blocker agent dissolved in said carrier host agent.

2. The medicament of claim 1 wherein said calmodulin blocker agent is trifluoperazine.

3. A method for topically, transdermally treating subdermal fibrotic tissue accumulation disorders, comprising the steps of:
   selecting a composition comprising:
      carrier host agent for transdermal delivery of a calmodulin blocker agent to an aberrant fibrotic tissue accumulation,
      calmodulin blocker agent dissolved in said carrier host agent;
   topically applying said composition to a bodily structure which exhibits symptoms of a subdermal fibrotic tissue accumulation disorder.

4. The method of claim 3 wherein said calmodulin blocker agent is trifluoperazine.

* * * * *